United States Patent [19]
Rothmel

[11] Patent Number: 5,516,688
[45] Date of Patent: May 14, 1996

[54] METHOD OF BIODEGRADING HYDROPHOBIC ORGANIC COMPOUNDS, PARTICULARLY PCBS, AND REMEDIATION THEREOF USING A BIOEMULSIFIER

[75] Inventor: Randi K. Rothmel, Mount Holly, N.J.

[73] Assignee: Envirogen, Inc., Lawrenceville, N.J.

[21] Appl. No.: 319,800

[22] Filed: Oct. 7, 1994

[51] Int. Cl.$^6$ .............................. B09B 3/00; B01F 17/00
[52] U.S. Cl. .................... 435/262.5; 435/253.3; 210/611; 252/351
[58] Field of Search .................. 435/41, 252.1, 435/253.6, 253.3, 262, 262.5; 210/610, 611; 252/351

[56] References Cited

U.S. PATENT DOCUMENTS

| | | | |
|---|---|---|---|
| 4,818,817 | 4/1989 | Shoham | 536/1.1 |
| 4,883,757 | 11/1989 | Gutnick | 435/252.1 |

OTHER PUBLICATIONS

Rothmel, R. R., Isolation And Characterization Of A New . . . Abstracts Gen Meet AM SOL Microbiol 93(0) 1993 p. 374.

Van Dyke M., Applications Of Microbial Surfactants, Biotech Adv vol. 9 pp. 241–252 1991.

Sundari R., Extracellular Microbial Lipids . . . J Environ Sci Health A 30(1) 171–182 (1995).

*Primary Examiner*—Ralph J. Gitomer
*Attorney, Agent, or Firm*—Miller & Christenbury

[57] ABSTRACT

The invention includes remediating a medium contaminated with an organohalide using a microorganism that produces a bioemulsifier. The organohalide is dispersed within the medium by contacting the medium with the bioemulsifier directly produced from *Pseudomonas cepacia* ATCC 55487 or obtained from a growth medium supernatant of *Pseudomonas cepacia* ATCC 55487. Then, the medium and the organohalide is treated with *Pseudomonas cepacia* ATCC 55487 which causes the organohalide to degrade in the presence of the Pseudomonas cepacia ATCC 55487.

15 Claims, 2 Drawing Sheets

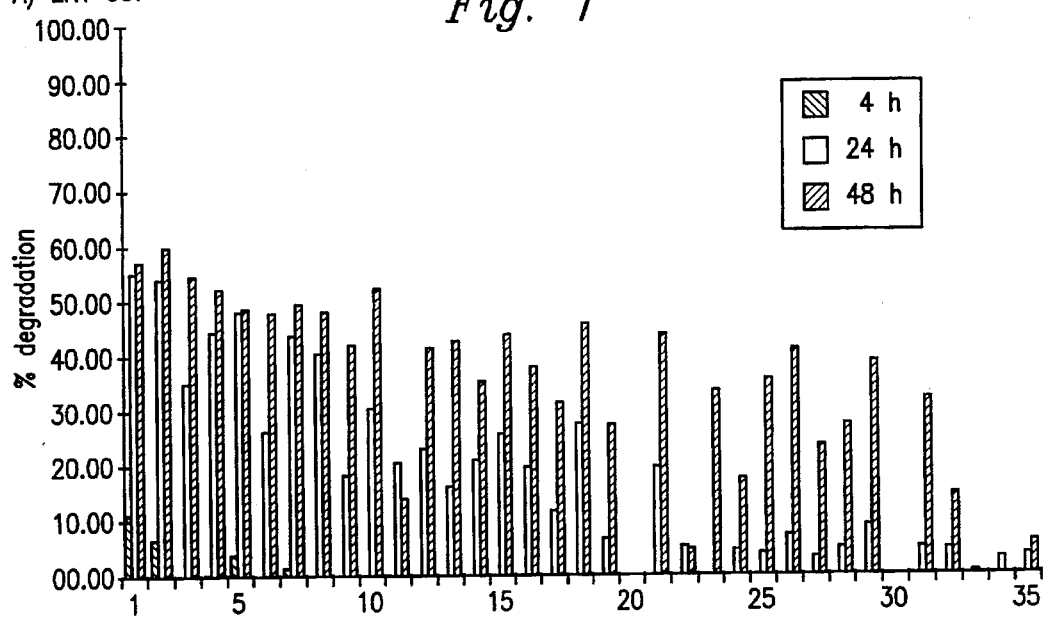
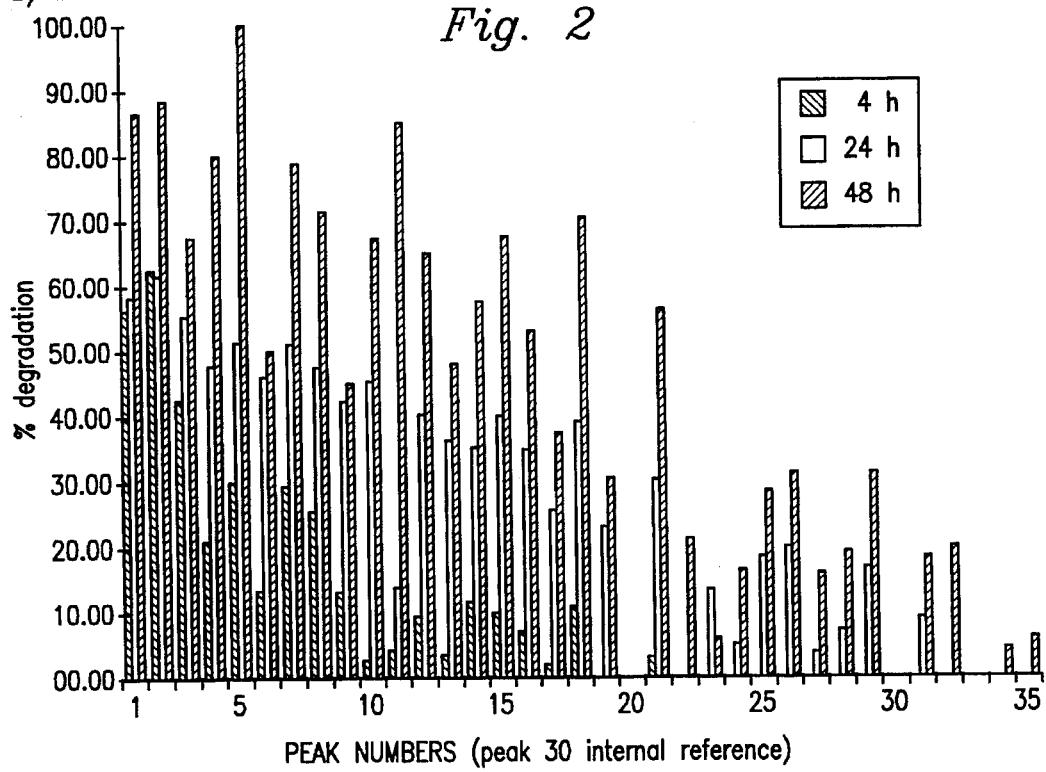
PEAK NUMBERS (peak 30 internal reference)

ENV 360 + ENV 391 biosurfactant
(71% degradation)

ENV 360 treatment
(57% degradation)

Aroclor 1248 control

METHOD OF BIODEGRADING HYDROPHOBIC ORGANIC COMPOUNDS, PARTICULARLY PCBS, AND REMEDIATION THEREOF USING A BIOEMULSIFIER

FIELD OF THE INVENTION

The present invention relates to a method of degrading organic waste material, particularly to a method of biodegrading hydrophobic hydrocarbon compounds such as polychlorobiphenyls.

BACKGROUND OF THE INVENTION

Hydrophobic organic compounds (HOCs), particularly polychlorobiphenyls (PCBs) and polyaromatic hydrocarbons (PAHs), are common environmental pollutants known for their toxicity and the health hazards presented when in contact with humans or other animals. Typical of HOCs are PCBs which include 2-chlorobiphenyl, 3-chlorobiphenyl and the like, polybromobiphenyls (PBBs), diphenylphenols, PAHs including naphthalene, fluorene, phenanthrene and the like. PCBs and other PAHs have been used commercially and industrially for a variety of purposes such as in electrical power transformers, as pesticides, as chemical components and the like. Leaky above or below ground storage tanks, improperly handled transformers, spills or improper disposal of waste materials containing PCBs and PAHs have polluted aquifers, soils, ground water, waste water and the like on a far ranging basis. This phenomenon is especially troublesome in the case of PCBs since PCBs resist degradation in the environment and accumulate in animal tissues over time. Moreover, such HOCs are typically hydrophobic and difficult to disassociate from the media in which they are located.

A number of techniques have been developed in attempts to degrade and remove PAHs, PCBs and related halogenated organic compounds from contaminated media. However, such techniques are typically quite limited in their flexibility of use and have proven to be less than effective under many conditions. Many of these efforts have concentrated in the microbial degradation of PAHs, PCBs and halogenated organic compounds. However, efforts to date have fallen short of the desire to cost effectively and completely remediate soils and/or contaminated ground water and/or waste materials. For example, some techniques are marginally effective and can result in remediation costs on the order of $500 per cubic yard or more.

It is typical of HOCs to have a relatively high affinity for soil and exhibit hydrophobic tendencies, both of which further complicates degradation of those PAHs. This problem is especially vexing when attempting to remediate soils and sediments which frequently contain a substantial quantity of water. The hydrophobic tendency and soil affinity frequently results in adherence of the contaminant to the medium in which the contaminant is located to the extent that large portions of the contaminant are virtually precluded from consumption by the microorganism. It has, therefore, been a difficult problem to identify a means in which a higher percentage of the contaminant is subjected to the degrading effects of the microorganisms by overcoming the natural soil affinity and hydrophobic tendencies of the contaminant in wet or damp media.

The biodegradation of PCBs has been under study for nearly twenty years. Many university and industrial laboratories have demonstrated that PCBs are metabolized by microorganisms. However, these organisms exhibit distinct differences. The most common aerobic organisms, as isolated from soils and sediments, are able to degrade 1, 2 or 3 chlorine atoms on the biphenyl nucleus. It is only exceptional organisms that have been shown to be able to degrade PCBs with 4, 5, 6, and even 7 chlorine atoms. These strains have been classified into several type strains (Type I–IV) based on their ability to degrade certain PCB congeners. Type IV strains, for example, produce a biphenyl dioxygenase that can attack PCBs at the 3, 4 ring positions as well as the standard 2, 3 sites. When this information is viewed in terms of commercial mixtures such as Aroclor, it is clear that only Aroclors 1221, 1242, and 1248 are currently amenable to direct aerobic biodegradation. Aroclors 1254 and 1260 are too highly chlorinated to be reasonably degraded by currently existing aerobic bacterial strains.

OBJECTS OF THE INVENTION

It is accordingly an object of the present invention to employ microorganisms in a method capable of degrading hydrophobic HOC compounds, especially PCBs, contained within a contaminated medium.

It is another object of the invention to provide a method of remediating a medium contaminated with hydrophobic hydrocarbon compounds which overcomes high soil affinity and the hydrophobic nature of the contaminant, despite the presence of water in the medium.

Other objects and advantages of the invention will become apparent to those skilled in the art from the drawings, the detailed description of preferred embodiments and the appended claims.

SUMMARY OF THE INVENTION

The invention includes a method of degrading HOCs, especially PCBs, with a unique microorganism, *Pseudomonas cepacia* ATCC 55487 (ENV 391) (sometimes hereinafter referred to as "ENV 391") that secretes its own bioemulsifier.

The invention also includes a method of producing the bioemulsifier by growing *Pseudomonas cepacia* ATCC 55487 (ENV 391) in a growth substrate, the *Pseudomonas cepacia* producing a bioemulsifier as a by-product. Then, a precipitate of the by-product is formed in the growth substrate by ammonium sulfate or acid precipitation. The redissolved precipitate is then extracted to produce pure bioemulsifier.

The invention also includes remediating a medium contaminated with a hydrophobic compound using a bioemulsifier obtained from the microorganism. The organohalide is dispersed within the medium by contacting the medium with the bioemulsifier obtained from a growth medium supernatant of *Pseudomonas cepacia* ATCC 55487. Then, the medium and the HOC are treated with *Pseudomonas cepacia* ATCC 55487 or other selected microorganism(s) which causes the HOC to degrade.

BRIEF DESCRIPTION OF THE DRAWINGS

FIGS. 1 and 2 graphically demonstrate percent degradation of peaks from Aroclor 1248 over time.

DETAILED DESCRIPTION OF THE INVENTION

Figure 3:
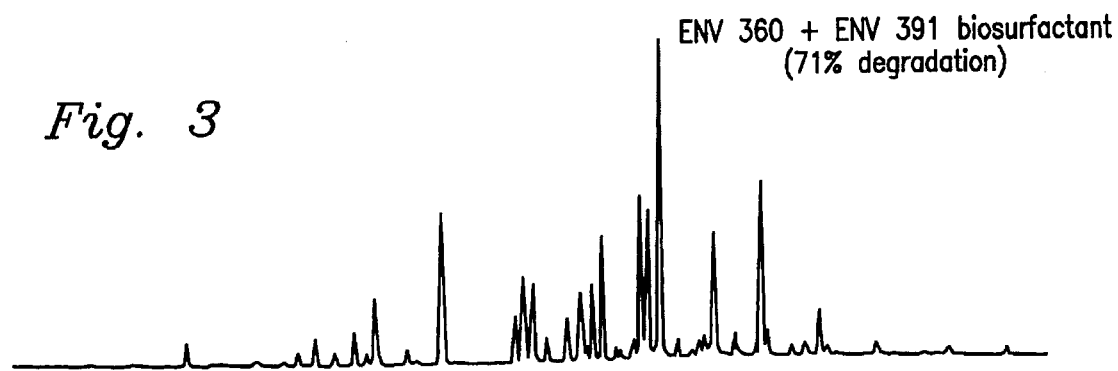
FIG. 3 is a chromatogram from a 20 ppm Aroclor 1248 assay using ENV 360 cells in a $1\times10^9$ cells/ml in 100 ml of 50× concentrated ENV 391 bioemulsifier solution demonstrating PCB degradation in accordance with aspects of the invention.

It will be appreciated that the following description is intended to refer to specific aspects of the invention selected for illustration in the drawings and the tables and is not intended to define or limit the invention other than in the appended claims.

Cultures of *Pseudomonas cepacia* discovered in connection with aspects of the invention have been deposited with the American Type Culture Collection, 12301 Parklawn Drive, Rockville, Md. 20852. The microorganism has been given the identifying ATCC number 55487. The organism shall be made available to the public in accordance with the terms of the Budapest Treaty.

Other microorganisms, *Pseudomonas pickettii* "ENV 307" and *Rhodococcus sp.* "ENV 360", are used herein for comparison purposes. Microbial studies previously have been conducted using two complementary PCB-degrading strains, for example ENV 307 and ENV 360. These strains demonstrate exceptional ability to degrade higher chlorinated PCB congeners (tetra-, penta-, hexa-) by utilizing the so-called 2, 3- and 3, 4-dioxygenase pathways. There is an additive effect of using these two PCB-degrading cultures for treating PCB contaminated soils, in contrast to using only one culture. Bacterial Enrichments using soils from selected sites have resulted in the isolation of several new bacterial strains that possess unique PCB-degrading activities. One of these strains, ENV 391, produces a bioemulsifier that has been associated with improved performance over the previously isolated comparable strain, ENV 307, in treating PCB-contaminated matrices.

The ENV 391 microorganism and the bioemulsifier it produces are employed for degrading PCBs and remediating contaminated media. The bioemulsifier can be employed in solubilizing other HOCs including chlorobenzoates, diphenyl phenols, and PAHs, such as naphthalene, fluorene, chrysene, phenanthrene, and the like. It has been discovered in the invention that the ENV 391 microorganism produces a bioemulsifier during growth. The bioemulsifier is particularly produced by growing ENV 391 in a growth substrate, which results in production of the bioemulsifier by ENV 391 as a byproduct. The bioemulsifier byproduct may be separated from the growth substrate supernatant by ammonium sulfate or acid precipitation. The precipitate is then redissolved in buffered water or dilute sodium bicarbonate and dialyzed against the dissolving buffer.

A wide variety of media may be remediated or decontaminated with the ENV 391 microorganism and its byproduct bioemulsifier. Selected examples of such media include soils, sludges, sediments, chemical wastes, dredge tailings and the like. Steps of the method of remediation or decontamination of a media contaminated with a HOC include contacting the medium with the bioemulsifier produced as a byproduct of growth of ENV 391 in a growth substrate, causing the bioemulsifier to contact the HOC and form an emulsion, thereby disengaging the HOC from the media, treating the HOG with ENV 391 or other selected microorganism and causing the HOG to degrade in the presence of the microorganism.

Another aspect of the invention is to contact a PCB-contaminated matrix with ENV 391 in a growth medium capable of supporting bioemulsifier production, causing the bioemulsifier to contact the PCB, thereby disengaging the PCB from the matrix, making the PCB available for degradation by ENV 391 and other PCB-degrading strains.

The growth substrate employed for the ENV 391 may be selected from any number of growth substrates such as glucose, galactose, rhamnose, succinic acid, dextrose, fructose, lactic acid, citric acid, glycerol, glutamine, and biphenyl. Other growth substrates may be employed, preferably so long as they are nontoxic and would not further contaminate the media to be remediated.

ENV 391 and its bioemulsifier may be used to remediate contaminated media in a variety of different ways, depending on the quantity and location of the contaminated media. For example, when the quantity of contaminated media is large, the media, such as soils, sediments and the like, may be transported to a decontamination container and subjected to remediation treatment. In other cases where it is impractical to remove contaminated media, such as large quantities of soil, the method may be used in situ, by introducing the microorganisms into the soil, introducing the growth substrate into the soil, thereby causing ENV 391 to produce the bioemulsifier which assists in degradation of the contaminants.

A number of studies were conducted and are described below. The experiments herein include isolation of the microorganism, production, precipitation and extraction of the bioemulsifier and showings of excellent degradation and remediation capabilities in accordance with the invention. It is fully within the scope of the invention to use the bioemulsifier in the presence of HOCs other than PCBs. In such cases, other HOC-degrading organisms may be used in applying the invention for degrading alternate HOCS. The microorganisms may be used singly or in combination, as desired. Various organisms that can be used in conjunction with this invention for treating a variety of HOCS include:

| Strain | Reference |
|---|---|
| PCB-degrading organisms | |
| Pseudomonas LB400 | Bopp, L. H., 1986, J. Ind. Microbiol., 1:23. |
| Alcaligenes eutrophus-H850 Corynebacterium Strain MB1 | Bedard, D. L., Wagner, R. E., Brennan, M. L., and Brown, J. F., Jr., 1987, Appl. Environ. Microbiol., 53:1094. |
| Acinetobacter Strain P6 | Furukawa, K., Tonomura, K., and Kamibayashi, A., 1978, Appl. Environ. Microbiol., 35:223. |
| Rhodococcus globerulus P6 | Astorias, J. A., and Timmis, K. N., 1993, J. Bacteriol., 175:4631 |
| Nocardia Sp. | Kilpi, S., Himberg, K., Yrjala, K., and Backstorn, V., 1988, FEMS Microbiol. Ecology, 53:19. |
| Pseudomonas Sp. | Barton, M. R., and Crawford, R. L., 1988, Appl. Environ. Microbiol. 54:594 |
| Pseudomonas Sp. Rhodococcus Sp. | Shannon, M. J. R., Rothmel, R., Chunn, C. D., and Unterman, R., 1994, Biodegradation of Chlorinated and Polycyclic Aromatic Hydrocarbon Compounds, Lewis Publishers, 354. |
| Bromo biphenyl-degrading strain | |
| Pseudomonas cruciviae | Takase, I., Omori, T., and Minoda, Y., 1986, Agric. Biol. Chem., 50:681. |
| Pentachlorophenol-degrading strains | |
| Rhodococcus chlorophenolicus | Apajalahti, J. H. A., and Salkinoja-Salonen, M. S., 1986, Appl. Microbiol. Biotechnol., 25:62 |

| Strain | Reference |
|---|---|
| *Mycobacterium Sp.* | Haggblom, M.., Nohynek, L. J., and Salkinoja-Salonen, M. S., 1988, Appl. Environ, Microbiol., 54:3043. |
| *Flavobacterium Sp.* | Brown, E. J., Pignatello, J. J., Martinson, M. M., and Crawford, R. L., 1986, Appl. Environ. Microbiol., 52:92. |
| PAH-degrading strains | |
| *Cunnighamella elegans* | Pothuluri, J. V., Freemen, J. P., Evans, F. E., and Cerniglia, C. E.,. 1992, Appl. Environ. Microbiol., 58:3654. |
| *Agmenellum quadruplicatum* | Narro, M. L., Cerniglia, C. E., VanBaalen, C., and Gibson, D. T., 1992, Appl. Environ. Microbiol., 58:1351. |
| *Oscillatoria Sp.* | Narro, M. L., Cerniglia, C. E., VanBaalen, C., and Gibson, D. T., 1992, Appl. Environ. Microbiol., 58:1360. |
| *Phanerochaete chrysosporium* | Bumpus, J. A., 1989, Appl. Environ. Microbiol., 55:154. |
| *Pseudomonas paucimobilis* | Mueller, J. G., Chapman, P. J., Blattmann, B. O., and Pritchard, P. H., 1990, Appl. Environ. Microbiol., 56:1079. |
| *Mycobacterium Sp.* | Heitkamp, M. A., and Cerniglia, C. E., 1989, Appl. Environ. Microbiol., 55:1968. |
| DDT-degrading strains | |
| *Alcaligenes eutrophus* A5 | Nadeau, L. J., Menn, F. M., Breen, A., and Sayler, G. S., 1994, Appl. Environ. Microbiol., 60:51. |

Study 1–Isolation of ENV 391

Bacterial enrichments using soils from selected sites were conducted to isolate new bacterial strains that possess unique PCB-degrading activities. A number of soils were chosen for enrichment purposes based on the PCB gas chromatograph (GC) profile of the soil extracts. Soils having PCB profiles that appeared to be transformed (altered) as compared to chromatogram(s) of pure contaminating Aroclor were chosen for enrichments. The reasoning was that the observed transformation may have been due to biological activity present in the soil. A list of soils used in several enrichment procedures is shown in Table 1. In all soil enrichments 10 to 20 ml of basal salts mineral (BSM) medium containing carbon sources was added to a small amount of soil (2–5 g). Once a week 1 ml of each soil slurry was removed and transferred to fresh BSM (10–20 ml) supplemented with an appropriate carbon source. After one standard transfer (in 2nd growth cycle) the following observation was made: the Pit 1 enrichment on chlorobiphenyl(s) appeared to make an emulsion on the sides of the growth vessel indicating the production of an emulsifier.

After 4 to 5 transfers, if growth was apparent in the BSM medium (turbidity), the cultures were passed onto BSM supplemented with biphenyl. Cultures were then grown to an optical density of $OD_{550}=1.0$ as read on a Spectronic 20™ spectrophotometer and assayed for PCB-degrading activity by an Aroclor 1248 assay. Such assays were performed as follows unless noted otherwise: 1 ml of selected culture $OD_{550}=1.0$ was incubated for 24 hours with 20 ppm (20 µ/ml final concentration) of Aroclor 1248 at 26° C. on loosely capped 2 gram vial. PCBs were then extracted with 2 ml of diethyl ether for 2 hours and analyzed using a gas chromatograph equipped with an electron capture detector. Results of selected initial Aroclor 1248 assays are presented in Table 2.

TABLE 1

| Sample | Enriched with* |
|---|---|
| L61A | A |
| L61X | A |
| L56V | A |
| C57S | A |
| G48L | A |
| Pit 1 | A,C |
| A51M | A,B,C |
| C51J | A,B,C |
| EB30 | A,B,C |
| Swale | A,B,C |

*A = 2-,3-,4-, and/or 4,4'-chlorobiphenyl; B = 2-,3-, and 4-chlorobenzoate (CBa); C = 2,6 diphenyl phenol (DPP)

TABLE 2

| Sample | Enriched with | % PCB degradation |
|---|---|---|
| L61A | 2-, and 4-CB | 34 |
| G48L | 2-, and 4-CB | 34 |
| C57S | 2-, and 4-CB | 38 |
| Pit 1* | 2-, and 4-CB | 48 |
| Swale | 2-,3-, and 4-CB | 20 |
| C51J | 2,6 DPP | 20 |
| C51J | 2-,3-,4-, CBa | 21 |
| EB30 | 2,6 DPP | 0 |

*This enrichment was used in further characterizations.

Of these representative enrichments only the Pit 1 mixed culture growing on 2-, and 4-CB maintained viability and PCB-degrading activity on subsequent transfers to BSM medium supplemented with either 2 CB or 4 CB. These mixed cultures were assayed with Aroclor 1248 (20 ppm for 72 hours). The results are shown in Table 3. The pattern of PCB degradation for these mixed cultures resembled that of another ENV isolate, ENV 307.

TABLE 3

| Sample | Enriched with | % PCB degradation |
|---|---|---|
| Pit 1 | 2CB | 77 |
| Pit 1 | 4CB | 75 |

Cultures from the 2 CB and 4 CB growth were diluted and plated onto tryptic soy agar plates (TSA). Individual colonies were picked and grown in BSM-Bp. This was repeated 2 or 3 times until a pure culture capable of growing on biphenyl was obtained. In addition, the pure culture was capable of growing on both 2 CB and 4 CB. The morphology of the pure isolate on TSA plates was as small transparent yellow colonies. This is in contrast to the ENV 307 phenotype—large white slimy colonies. The culture showed between 60 and 65% PCB degradation in an Aroclor 1248 assay. Gram stain of the culture indicated that the microorganism was a gram negative rod. However, the gram stain result was somewhat variable. The purified culture was analyzed for fatty acid and the results are shown in Table 4. The similarity index indicates the degree of similarity between the unknown sample and the fatty acid data base available from known species. A value of 1.0 would be an exact match to a defined organism. From the fatty acid analysis, it is 73% certain that this organism is a *Pseudomonas cepacia*. This organism was designated *Pseudomonas cepacia* ENV 391.

TABLE 4

A) Lipid analysis of ENV 391

| Fatty acid composition | Weight percent (%) |
| --- | --- |
| 14:0 | 3.99 |
| Mixture (peak 2)[1] | 4.87 |
| 16:1 cis 9 | 19.65 |
| 16:0 | 22.22 |
| 17:0 cyclo | 6.75 |
| 16:1 2 OH | 1.21 |
| 16:0 2 OH | 1.39 |
| 16:0 3 OH | 3.93 |
| Mixture (peak 8)[1] | 30.82 |
| 18:0 | 0.78 |
| 19:0 cyclo C11-12 | 4.39 |

B) Similarity index

| Microorganism | Similarity index |
| --- | --- |
| *Pseudomonas cepacia* | 0.732 |
| *Ps. cepacia* GC subgroup B | 0.732 |
| *Ps. cepacia* GC subgroup A | 0.491 |
| *Ps. galadioli* | 0.491 |

[1]These peaks are comprised of a mix of individual fatty acid components.

Study 2—Characterization of ENV 391

Having identified a microorganism (ENV 391) from Pit 1 as having high degradative activity, a comparative analysis between ENV 391 and ENV 307 was undertaken. Both organisms were grown in BSM, supplemented with a variety of carbon sources (see Table 5) to determine the carbon utilization of each strain.

TABLE 5

| Carbon source | ENV 307 | ENV 391 |
| --- | --- | --- |
| biphenyl | yes (24 h) | yes (24 h) |
| 2-chlorobiphenyl | yes (24 h) | yes (24 h) |
| 4-chlorobiphenyl | yes (48–72 h) | yes (24 h) |
| glucose | no | yes (24 h) |
| galactose | yes (48 h) | yes (48 h) |
| rhamnose | no | yes (48 h) |
| sucrose | no | no |
| succinic acid | yes (24 h) | yes (24 h) |
| dextrose | yes (48 h) | yes (24 h) |
| fructose | yes (24 h) | yes (48 h) |
| lactose | no | no |
| lactic acid | yes | yes |
| citric acid | yes (24 h) | yes (48 h) |

A comparison of degradation rates of ENV 391 versus ENV 307 was then conducted using Aroclor 1248 to determine which microorganism had better degradation capabilities. ENV 307 and ENV 391 were grown in biphenyl (Bp) and basal salts medium (BSM) to ~1.00 D. The cells were spun and resuspended in fresh BSM to OD=1 and subjected to Aroclor 1248 assays. The assays were set up as follows:

A) 1 ppm for 1 hr, 4 hr, 24 hr and 48 hr

B) 10 ppm for 1 hr, 4 hr, 24 hr and 48 hr

C) 20 ppm for 1 hr, 4 hr, 24 hr and 48 hr

Three vials were set up for both cell strains for all incubation times and concentrations. One vial in each set was killed by adding 10 μl of $H_2SO_4$. The other two vials were duplicate experimental vials. After incubating for 1, 4, 24 or 48 hours the reaction was stopped (in the experimentals) by adding 10 μl of $H_2SO_4$. The assays were extracted with 2 ml ether except for the 1 ppm samples which were extracted with 1 ml. The ppb for peak 28, the internal standard a non-degradable PCB congener, was determined from the resulting chromatograms and a ratio was taken against total ppb. The killed control (e.g. 307K) ratio was used to determine the percent degradation from the test ratios. The results for the 10 ppm assay are shown graphically in FIGS. 1 & 2. As indicated, ENV 391 is capable of degrading PCB congeners at a faster rate and to a more extensive level than that of ENV 307.

Study 3—PCB degradation in soil—ENV 391 vs. ENV 307

As shown in the previous study ENV 391 degraded PCB congeners at a faster rate and to a more extensive level than that of ENV 307. A comparison of these two strains in a soil environment was then made. Equivalent amounts of ENV 307 and ENV 360 or ENV 391 and ENV 360 were used to treat soil contaminated with 35 ppm of Aroclor 1248. The results (Table 6) show that there was more PCB degradation using the bacterial combination ENV 391+ENV 360 as compared to ENV 307+ENV 360 in a one day soil treatment.

TABLE 6

| Treatment | % PCB degradation |
| --- | --- |
| ENV 391 + ENV 360 | 66.0 |
| ENV 307 + ENV 360 | 41.7 |

Study 4—Identification and Purification of ENV 391 Bioemulsifier

It was hypothesized that the observed enhanced activity of ENV 391 as compared to ENV 307 was due to the production of a bioemulsifier. This was first evident during the isolation of ENV 391, when an emulsion was apparent during bacterial enrichments. A solubilization test was conducted with Aroclor 1248 oil using bacterial supernatants and partially purified ENV 391 bioemulsifier to determine the presence of emulsifying activity. One ml of a growth medium supernatant (ENV 307, ENV 391, or ENV 360) or partially purified ENV 391 bioemulsifier was added to a droplet of Aroclor 1248. The supernatant/Aroclor mixes were vortexed for one minute and the degree of emulsification monitored over a 24 hour period. The amount of emulsification was determined by visual comparison of the extent of dispersion of Aroclor 1248 droplets. The amount of emulsification was defined as indicated in Table 7.

TABLE 7

| | |
| --- | --- |
| − | No PCB droplets dispersion after 1 hr. |
| +/− | Initially observed PCB droplet dispersion that coalesced into 1–5 droplets with 24 hr. |
| + | Slight PCB dispersion |
| +/+ | Moderate PCB dispersion |
| +/+/+ | Excellent PCB dispersion |

In this experiment, the bioemulsifier was partially purified from cells grown to various optical densities, as measured by light scattering at a wavelength of 550 nm using a Spectronic 20™ spectrophotometer. ($OD_{550}$=1 was determined to be approximately equal to $1\times10^9$ cells per ml.) The suspected bioemulsifier was partially purified from a growth medium supernatant of ENV 391 grown cells ($OD_{550}$=25) by either ammonium sulfate precipitation or by acid precipitation. In the ammonium sulfate precipitation procedure, $NH_4SO_4$ was slowly added to the cell-free supernatant to 60% saturation. The precipitate that formed was collected by centrifugation, redissolved in $dH_2O$ and dialyzed. In the acid precipitation procedure, 10% $H_2SO_4$ acid was slowly added to the cell-free supernatant while mixing until pH 2 was reached. The precipitate that formed was collected by centrifugation, redissolved in sodium bicarbonate and extracted with chloroform/ethanol (2:1). The aqueous fraction contained the emulsifying activity. Both resulting partially purified bioemulsifier preparations for ENV 391 were concentrated fifty fold as compared to the original growth supernatant. The results shown in Table 8 indicated the presence of a bioemulsifier in the supernatant of ENV 391 cells, which could be partially purified by either ammonium sulfate precipitation or acid precipitation.

TABLE 8

| Sample | Degree of Emulsification |
| --- | --- |
| ENV 307 ($OD_{550}$) = 1 | − |
| ENV 307 ($OD_{550}$) = 1 | +/− |
| ENV 360 ($OD_{550}$) = 1 | − |
| ENV 360 ($OD_{550}$) = 1 | +/− |
| ENV 391 ($OD_{550}$) = 1 | + |
| ENV 391 ($OD_{550}$) = 25 | +/+ |
| ENV 391 Bioemulsifier 50X concentrated by | |
| a) ammonium sulfate precipitation | +/+/+ |
| b) acid precipitation | +/+/+ |

No bioemulsifier was produced by either of ENV 307 or ENV 360.

Evidence for production of a bioemulsifier was further demonstrated in an Aroclor 1248 assay. ENV 360, ENV 307 and ENV 391 cells were incubated under standard conditions in an Aroclor 1248 assay either in the presence or absence of partially purified ENV 391 bioemulsifier. Twenty microliters of the partially purified bioemulsifier (50×concentration) was added to the 1 ml assays as indicated in Table 9. The bioemulsifier was purified as follows. ENV 391 cell were grown to an $OD_{550}$=25. The biomass was then pelleted by centrifugation and 390 g of ammonium sulfate was slowly added to 1 L of the growth supernatant (60% $NH_4SO_4$ saturation) while stirring. The precipitant that formed was collected by centrifugation and redissolved in buffered distilled water (pH 7.0) and was dialyzed against buffered distilled water.

TABLE 9

| Cell Type | Bioemulsifier (50X concentration) | % PCB degradation |
| --- | --- | --- |
| Killed Control | — | 0 |
| ENV 360 | — | 58 |
| ENV 360 | 20 μl | 71 |
| ENV 391 | — | 65 |
| ENV 391 | 20 μl | 69 |
| ENV 307 | — | 48 |
| ENV 307 | 20 μl | 53 |

Figure 4:
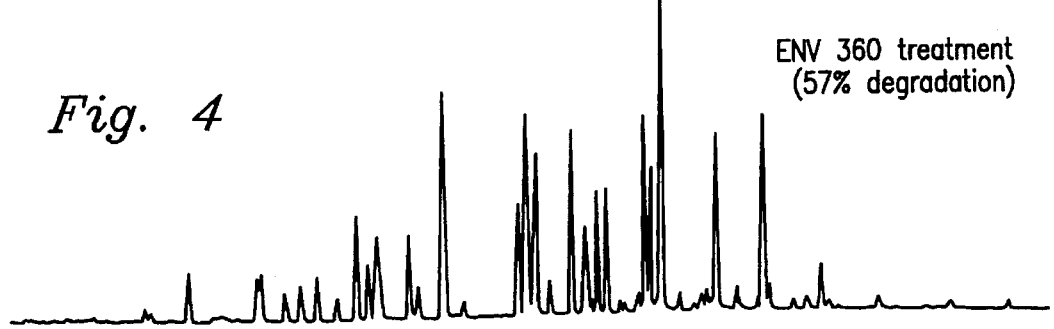
FIG. 4 is a chromatogram of a 20 ppm Aroclor 1248 assay without ENV 391 bioemulsifier solution.
Figure 5:
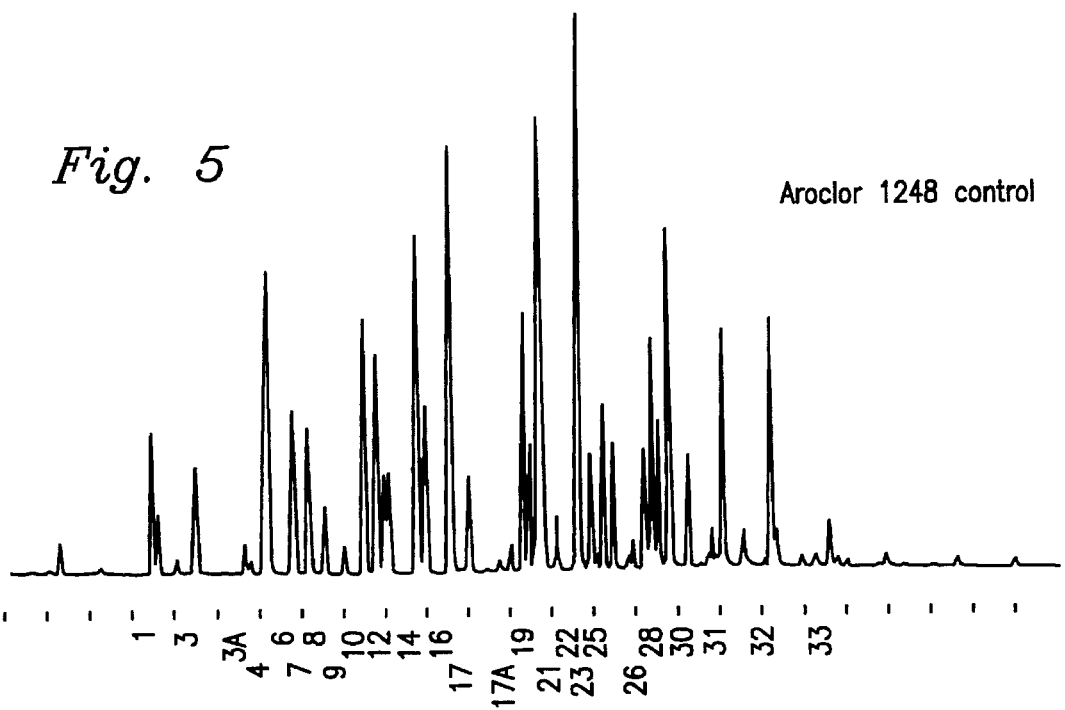
FIG. 5 is a chromatogram of a killed control Aroclor 1248 assay.

The presence of the suspected bioemulsifier greatly enhanced the PCB degrading activity of ENV 360 as shown in Table 9 and FIGS. 3–5, but did not enhance the activity of ENV 391 or ENV 307.

Study 5—Application of Bioemulsifier

The next set of experiments were conducted to assess the effectiveness of using the ENV 391 bioemulsifier to enhance remediation of PCB-contaminated soils.

ENV 391 bioemulsifier or control media (water or ENV 307 growth supernatant) was incubated with two soil types contaminated with Aroclor 1248. Both soil types were contaminated with between 650 and 700 ppm PCB. One to two grams of soil were mixed for one to two hours with 1 ml (final volume) of a media containing bioemulsifier or control as indicated in Table 10. The soil was collected by centrifugation. The soil fraction and 0.5 ml of the clear supernatant fraction were analyzed for PCB content. The amount of PCB solubilization is summarized below. Mixing soil with the ENV 391 bioemulsifier resulted in enhanced PCB solubilization (to varying amounts) depending on soil type.

TABLE 10

| | bioemulsifier addition | | Soil (μg PCB) | Supernatant (μg PCB) | % PCB Solubilization |
| --- | --- | --- | --- | --- | --- |
| Soil Type | Source | Amount added | | | |
| A | water control | — | 679 | 0.24 | 0.04 |
| A | water control | — | 752 | 0.12 | 0.02 |
| A | 391 (50X)* | 0.1 ml | 5920 | 4.2 | 0.71 |
| A | 391 (50X)* | 0.1 ml | 460 | 1.4 | 0.30 |
| A | 391 (50X)* | 1.0 ml | 437 | 7.4 | 0.84 |
| A | 391 (50X)* | 1.0 ml | 396 | 8.0 | 1.7 |
| B | water control | — | 624 | 0.46 | 0.07 |
| B | 391 supernatant** | 1.0 ml | 777 | 8.02 | 1.0 |
| B | 391 (50X)* | 1.0 ml | 375 | 98.5 | 21 |
| B | 307 supernatant** | 1.0 | 765 | <0.2 | <0.03 |

*The 391 (50X) bioemulsifier was from a partially purified sample ($NH_4SO_4$) at a 50X concentration.
**The 391 and 307 supernatants were from unpurified growth supernatants from cells grown to between $OD_{550}$ = 25 and 30.

Since the ENV 391 bioemulsifier was capable of solubilizing soil PCBs it was tested for its ability to enhance biodegradation in a soil treatability study. Two grams of PCB contaminated soil (Aroclor 1248; 300 ppm) was incubated with bioemulsifier (at varying concentrations) in a final volume of 2 ml for 1–2 hours. Experimental samples were then inoculated with ENV 391 and ENV 360 at a final concentration of 1×10$^9$ cells per ml and BSM was added to control samples. The final volume of the soil slurry was 10 ml (20% solids concentration). These soil slurries were incubated for three days prior to PCB analysis. Results are shown in Table 11. Addition of the bioemulsifier produced by ENV 391 improves PCB degradation from about 40% to 60% over the three day incubation when used as a 50× concentrated solution or diluted 1:10.

TABLE 11

| Sample | Bioemulsifier (50X concentration) added | % PCB degradation |
| --- | --- | --- |
| Control | — | 0 |
| Control | — | 0 |
| Control | 2.0 ml | 0 |
| Control | 0.2 ml | 0 |
| Control | 0.1 ml | 0 |
| Experimental | — | 40 |
| Experimental | 2 ml | 56 |
| Experimental | 0.2 ml | 60 |
| Experimental | 0.1 ml | 48 |

Although this invention has been described in connection with specific forms thereof, it will be appreciated that a wide variety of equivalents may be substituted for the specific elements described herein without departing from the spirit and scope of this invention as described in the appended claims. For example, although the examples have been directed primarily toward samples of soil, contaminated media can include sludges, sediments, chemical wastes, dredge tailings and the like, together with mixtures thereof.

The invention includes remediating a medium contaminated with an organohalide using a bioemulsifier obtained from the microorganism. The organohalide is dispersed within the medium by contacting the medium with the bioemulsifier obtained from a growth medium supernatant of *Pseudomonas cepacia* ATCC 55487. Then, the medium and the organohalide is treated with *Pseudomonas cepacia* ATCC 55487 which causes the organohalide to degrade in the presence of the *Pseudomonas cepacia* ATCC 55487.

What is claimed is:

1. A method of remediating a medium contaminated with a polyaromatic hydrocarbon comprising:

contacting said medium with a PCB-degrading microorganism *Pseudomonas cepacia* ATCC 55487 and inducing production of a bioemulsifier from *Pseudomonas cepacia* ATCC 55487; and remediating said medium by causing said polyaromatic hydrocarbon to degrade in the presence of said bioemulsifier.

2. The method defined in claim 1 wherein said polyaromatic is a pollutant in said medium.

3. The method defined in claim 2 wherein said medium is selected from the group consisting of soil, sludge, sediment, chemical waste and dredge tailings.

4. The method defined in claim 3 wherein said bioemulsifier is obtained by a process comprising forming a precipitate by ammonium sulfate or acid precipitation from said growth substrate, redissolving the precipitate and extracting the redissolved precipitate to form the bioemulsifier.

5. A method of producing a purified bioemulsifier comprising:

growing *Pseudomonas cepacia* ATCC 55487 in a growth substrate, said *Pseudomonas cepacia* producing a bioemulsifier as a by-product;

forming a precipitate of said by-product in said growth substrate by ammonium sulfate or acid precipitation;

redissolving the precipitate; either dialyzing the redissolved precipitate, or extracting it with a chloroform and ethanol mixture; and recovering purified bioemulsifier.

6. The method in claim 5 wherein said precipitate is redissolved in buffered water or dilute sodium bicarbonate.

7. A method of remediating a medium contaminated with a polyaromatic hydrocarbon comprising:

contacting said medium with a bioemulsifier produced as a by-product of growth of *Pseudomonas cepacia* ATCC 55487 in a growth substrate;

causing said bioemulsifier to contact said polyaromatic hydrocarbon and form an emulsion, thereby releasing said polyaromatic hydrocarbon from said medium;

treating said polyaromatic hydrocarbon with said *Pseudomonas cepacia* ATCC 55487 or another hydrophobic organic compound degrading microorganism and remediating said medium by causing said polyaromatic hydrocarbon to degrade in the presence of said bioemulsifier produced by *Pseudomonas cepacia* ATCC 55487.

8. The method defined in claim 7 wherein said growth substrate is selected from the group consisting of glucose, galactose, rhamnose, succinic acid, dextrose, fructose, lactic acid, citric acid, glycerol and glutamine.

9. The method defined in claim 7 wherein said polyaromatic hydrocarbon is a halogenated biphenyl.

10. The method defined in claim 9 wherein said halogenated biphenyl is a polychlorinated biphenyl.

11. The method defined in claim 7 wherein said polyaromatic hydrocarbon is selected from the group consisting of diphenyl phenol, polychlorinated biphenyls, polybromobiphenyls, naphthalene, fluorene and phenanthrene.

12. A method of remediating a medium contaminated with an organohalide comprising:

causing said organohalide to disperse within said medium by contacting said medium with a bioemulsifier obtained from a growth medium supernatant of *Pseudomonas cepacia* ATCC 55487;

treating said medium and said organohalide with a microorganism different from *Pseudomonas cepacia* ATCC 55487 and capable of degrading said organohalide; and remediating said medium by causing said organohalide to degrade in the presence of said microorganism.

13. The method defined in claim 12 wherein said microorganism is selected from the group consisting of Pseudomonas LB400; *Alcaligenes eutrophus*-H850; Corynebacterium Strain MB1; Acinetobacter Strain P6; *Rhodococcus globerulus* P6; *Nocardia Sp.; Pseudomonas sp.; Rhodococcus Sp.; Pseudomonas cruciviae; Rhodococcus chlorophenolicus; Mycobacterium Sp.; Flavobacterium Sp.; Cunnighamella elegans; Agmenellum quadruplicatum; Oscillatoria Sp.; Phanerochaete chrysosporium; Pseudomonas paucimobilis; Mycobacterium Sp.* and *Alcaligenes eutrophus* A5.

14. A method of remediating a medium contaminated with a hydrophobic organic compound comprising:

inducing production of a bioemulsifier from *Pseudomonas cepacia* ATCC 55487;

contacting said bioemulsifier in the presence of a microorganism selected from the group consisting of Pseudomonas LB400; *Alcaligenes eutrophus*-H850; Corynebacterium Strain MB 1; Acinetobacter Strain P6; *Rhodococcus globerulus* P6; *Nocardia Sp.; Pseudomonas Sp.; Rhodococcus Sp.; Pseudomonas cruciviae; Rhodococcus chlorophenolicus; Mycobacterium Sp.; Flavobacterium Sp.; Cunnighamella elegans; Agmenellum quadruplicatum; Oscillatoria*

*Sp.; Phanerochaete chrysosporium; Pseudomonas paucimobilis; Mycobacterium Sp.* and *Alcaligenes eutrophus* A5; and remediating said medium by causing said hydrophobic organic compound to degrade in the presence of said bioemulsifier and said microorganism.

15. A purified bioemulsifier comprising a byproduct produced by growing *Pseudomonas cepacia* ATCC 55487 in a growth substrate and then isolating said byproduct from said *Pseudomonas cepacia* ATCC 55487 and said growth substrate.

* * * * *

UNITED STATES PATENT AND TRADEMARK OFFICE
CERTIFICATE OF CORRECTION

PATENT NO. : 5,516,688

DATED : May 14, 1996

INVENTOR(S) : Randi K. Rothmel

Page 1 of 3

It is certified that error appears in the above-indentified patent and that said Letters Patent is hereby corrected as shown below:

On the title page: Item [54] and Col. 1, line 2, please change "METHOD OF BIODEGRADING HYDROPHOBIC ORGANIC COMPOUNDS, PARTICULARLY PCBS, AND REMEDIATION THEREOF USING A BIOEMULSIFIER" TO --METHOD OF BIODEGRADING HYDROPHOBIC ORGANIC COMPOUNDS, PARTICULARLY PCB'S, IN THE PRESENCE OF PSEUDOMONAS CEPACIA--;

under [56] "OTHER PUBLICATIONS", line 1, please change "Rothmel, R. R.," to --Rothmel, R. K.,--; and under [57] "ABSTRACT", line 10, please change "Pseudomonas cepacia" to --*Pseudomonas cepacia*--.

In Column 3, line 61, please change "HOG" to --HOC--; and line 62, please change "HOG" to --HOC--.

In Column 4, line 49, in the table, please change "Astorias" to --Asturias--.

In Column 5, line 64, please change "(20 u/ml" to --(20 µg/ml--; and
line 65, please change "C." to --C--.

In Column 6, line 35, please change "2 CB or 4 CB" to --2CB or 4CB--.

In Column 7, line 55, please change "~1.00 D." to --~1.0 OD.--.

UNITED STATES PATENT AND TRADEMARK OFFICE
CERTIFICATE OF CORRECTION

PATENT NO. : 5,516,688
DATED : May 14, 1996
INVENTOR(S) : Randi K. Rothmel

It is certified that error appears in the above-indentified patent and that said Letters Patent is hereby corrected as shown below:

In Column 8, line 22, please change "391+ENV" to --391 + ENV--; and
line 23, please change "307+ENV" to --307 + ENV--.

In Column 9, line 25, in Table 8, please change "concentrated by          " to --concentrated by--.

In Column 11, line 48, after "matic" please insert --hydrocarbon--.

UNITED STATES PATENT AND TRADEMARK OFFICE
CERTIFICATE OF CORRECTION

PATENT NO. : 5,516,688
DATED : May 14, 1996
INVENTOR(S) : Randi K. Rothmel

It is certified that error appears in the above-indentified patent and that said Letters Patent is hereby corrected as shown below:

In Column 12, line 14, please change "microorganism" to --microorganism;--;
line 45, please change "Pseudomonas" to --*Pseudomonas*--;
line 46, please change "Corynebacterium" to --*Corynebacterium*-- and change "Acinetobacter" to --*Acinetobacter*--;
line 61, please change "Pseudomonas" to --*Pseudomonas*--; and
line 62, please change "Corynebacterium" to --*Corynebacterium*--, change "MB 1" to --MB1-- and change "Acinetobacter" to --*Acinetobacter*--.

Signed and Sealed this

Fifteenth Day of October, 1996

Attest:

BRUCE LEHMAN

*Attesting Officer*  *Commissioner of Patents and Trademarks*